United States Patent
Aguirre Vargas et al.

(10) Patent No.: US 12,327,617 B2
(45) Date of Patent: Jun. 10, 2025

(54) HYBRID MACHINE LEARNING METHODS OF TRAINING AND USING MODELS TO PREDICT FORMULATION PROPERTIES

(71) Applicant: Dow Global Technologies LLC, Midland, MI (US)

(72) Inventors: Fabio Aguirre Vargas, Lake Jackson, TX (US); Sukrit Mukhopadhyay, Midland, MI (US); Jerome Claracq, Ghent (BE); Bart Rijksen, Middelburg (NL); Valeriy V. Ginzburg, Midland, MI (US); Paul Cookson, Cheadle (GB); Alix Schmidt, Midland, MI (US); Shachit Shankaran Iyer, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 18/085,318

(22) Filed: Dec. 20, 2022

(65) Prior Publication Data

US 2024/0203537 A1    Jun. 20, 2024

(51) Int. Cl.
*G16C 20/30* (2019.01)
*G16C 20/70* (2019.01)

(52) U.S. Cl.
CPC ............. *G16C 20/30* (2019.02); *G16C 20/70* (2019.02)

(58) Field of Classification Search
None
See application file for complete search history.

(56) References Cited

U.S. PATENT DOCUMENTS

| 10,984,145 B1 | 4/2021 | Hutchinson et al. |
| 2015/0148514 A1* | 5/2015 | Makal .............. G16C 20/30 528/85 |

(Continued)

FOREIGN PATENT DOCUMENTS

| CN | 111816266 | 10/2020 |
| CN | 113533133 | 2/2022 |

(Continued)

OTHER PUBLICATIONS

Allahawiah, "The impact of social networks in influencing the consumer purchasing decision via the internet: Analytical study in Albalqa Applied University", International Journal of Computer Applications, 2018, vol. 96, No. 23, pp. 0975-8887.

(Continued)

*Primary Examiner* — Yoshihisa Ishizuka

(57) ABSTRACT

Methods include training a machine learning module to predict one or more target product properties for a prospective chemical formulation, including (a) constructing or updating a training data set from one or more variable parameters; (b) performing feature selection on the training data set; (c) building one or more machine learning models using one or more model architectures; (d) validating the one or more machine learning models; (e) selecting at least one of the one or more machine learning models and generating prediction intervals; (g) interpreting the one or more machine learning models; and (h) determining if the one or more target product properties calculated are acceptable and deploying one or more trained machine learning models, or optimizing the one or more machine learning models by repeating steps (b) to (g). Methods also include application of trained machine learning modules to predict formulation properties from prospective data.

20 Claims, 3 Drawing Sheets

(56) References Cited

U.S. PATENT DOCUMENTS

| | | | |
|---|---|---|---|
| 2018/0172667 A1* | 6/2018 | Noskov | G16C 20/30 |
| 2021/0027864 A1* | 1/2021 | Plumbley | G16C 20/30 |
| 2021/0241848 A1* | 8/2021 | Tao | G16H 50/50 |
| 2022/0165364 A1* | 5/2022 | Qiao | G06N 3/044 |
| 2022/0237264 A1* | 7/2022 | Johansson | G06F 18/2135 |
| 2022/0397886 A1* | 12/2022 | Hong | G16C 20/10 |

FOREIGN PATENT DOCUMENTS

| | | |
|---|---|---|
| JP | 2022013310 | 1/2022 |
| WO | 2021111232 | 6/2021 |

OTHER PUBLICATIONS

Choi, "A Development of Defeat Prediction Model Using Machine Learning in Polyurethane Foaming Process for Automotive Seat", Journal of the Korea Academia-Industrial cooperation Society, 2021, vol. 22, iss. 6, pp. 36-42.

Engels, "Polyurethanes: Versatile Materials and Sustainable Problem Solvers for Today's Challenges", Angew. Chem., 2013, vol. 52, pp. 9422-9441.

Herrington, "Flexible Polyurethane Foams", The Polyurethane Book, John Wiley & Sons, 2002, chapters 2, 3, 6, 7 and 8.

Menon, "Hierarchical Machine Learning Model for Mechanical Property Predictions of Polyurethane Elastomers From Small Datasets", Front. Mater., 2019.

Okafor, "Evaluation of machine learning methods in predicting optimum tensile strength of microwave post-cured composite tailored for weight-sensitive applications", Engineering Science and Technology, an International Journal, 2022, vol. 25, iss. 100985.

Schubert, "Applying machine learning to predict the tensile shear strength of bonded beech wood as a function of the composition of polyurethane prepolymers and various pretreatments", Wood Science and Technology, 2020, vol. 54, iss. 1, pp. 19-29.

Tesser, "Modeling of Polyurethane Foam Formation", Journal of Applied Polymer Science, 2004, vol. 92, 1875.

Yang, "Comparative Study of Machine Learning Approaches for Predicting Creep Behavior of Polyurethane Elastomer", Polymers, 2021, vol. 13, 1768.

* cited by examiner

HYBRID MACHINE LEARNING METHODS OF TRAINING AND USING MODELS TO PREDICT FORMULATION PROPERTIES

FIELD

Embodiments relate to methods of predicting target product properties for a prospective chemical formulation using a machine learning module and methods of training machine learning modules.

INTRODUCTION

The design of chemical formulations across industries often involves combining various chemical components to generate a product having one or more target properties through labor intensive methodologies that can involve high throughput serial and parallel experimentation. However, as the scale and complexity of the chemical formulations increase, to optimize the product target properties, the number of combinations and experiments needed to map the chemical parameter space increases exponentially. This has led to the development of computer-based approaches that utilize machine learning from volumes of historical formulation data to predict target product properties given a formulation composition and process conditions as input.

Machine learning approaches to formulation design often require larger data sets of historical information to generate accurate predictive model and minimize overfitting. However, increasing the number of components and/or classes within the data set (dimensionality), exponentially increases the number of interactions that must be considered. A number of methodologies have been developed that consider only component relationships, which require large training data sets and can produce inaccurate predictions when formulation components that are non-representative of the training data are included. Further, other methods that rely on the use of components and formulation descriptors can lead to oversimplification and ultimately decrease the accuracy of target product property prediction.

SUMMARY

In an aspect, methods may include a machine learning module to predict one or more target product properties for a prospective chemical formulation, including: (a) constructing or updating a training data set to train one or more models using machine learning from one or more variable parameters comprising one or more of chemical components, descriptors, process conditions, and the one or more target product properties; (b) performing feature selection on the training data set to determine a subset of driving variable parameters for calculating the one or more target product properties; (c) building one or more machine learning models using one or more model architectures and analyze the training data set and subset of driving variable parameters used in calculating the one or more target product properties; (d) validating the one or more machine learning models by inputting a testing data set and determining an associated error for the one or more machine learning models calculating the one or more target product properties; (e) selecting at least one of the one or more machine learning models and generating prediction intervals for the one or more machine learning models using a bootstrapping method; (f) interpreting the one or more machine learning models and analyzing the one or more target product properties calculated by the one or more machine learning models; and (g) determining if the one or more target product properties calculated by the one or more machine learning models are acceptable and deploying one or more trained machine learning models, or optimizing the one or more machine learning models by repeating steps (b) to (f).

In another aspect, methods may include determining one or more target product properties from a prospective chemical formulation, including: inputting the prospective chemical formulation into a machine learning module, wherein training the trained machine learning models includes: (a) constructing or updating a training data set from one or more variable parameters to train one or more models using machine learning comprising one or more of chemical components, descriptors, process conditions, and the one or more target product composition properties; (b) performing feature selection on the training data set to determine a subset of driving variable parameters for calculating the one or more target product properties; (c) building one or more machine learning models using one or more model architectures and analyze the training data set and subset of driving variable parameters used in calculating the one or more target product properties; (d) validating the one or more machine learning models by inputting a testing data set and determining an associated error for the one or more machine learning models calculating the one or more target product properties; (e) selecting at least one of the one or more machine learning models and generating prediction intervals for the one or more machine learning models using a bootstrapping method; (f) interpreting the one or more machine learning models and analyzing the one or more target product properties calculated by the one or more machine learning models; (g) determining if the one or more target product properties calculated by the one or more machine learning models are acceptable and deploying one or more trained machine learning models, or optimizing the one or more machine learning models by repeating steps (b) to (f); inputting a selection of one or more target product properties to be predicted into the machine learning module; and outputting the one or more predicted target product properties.

DETAILED DESCRIPTION

Figure 1:
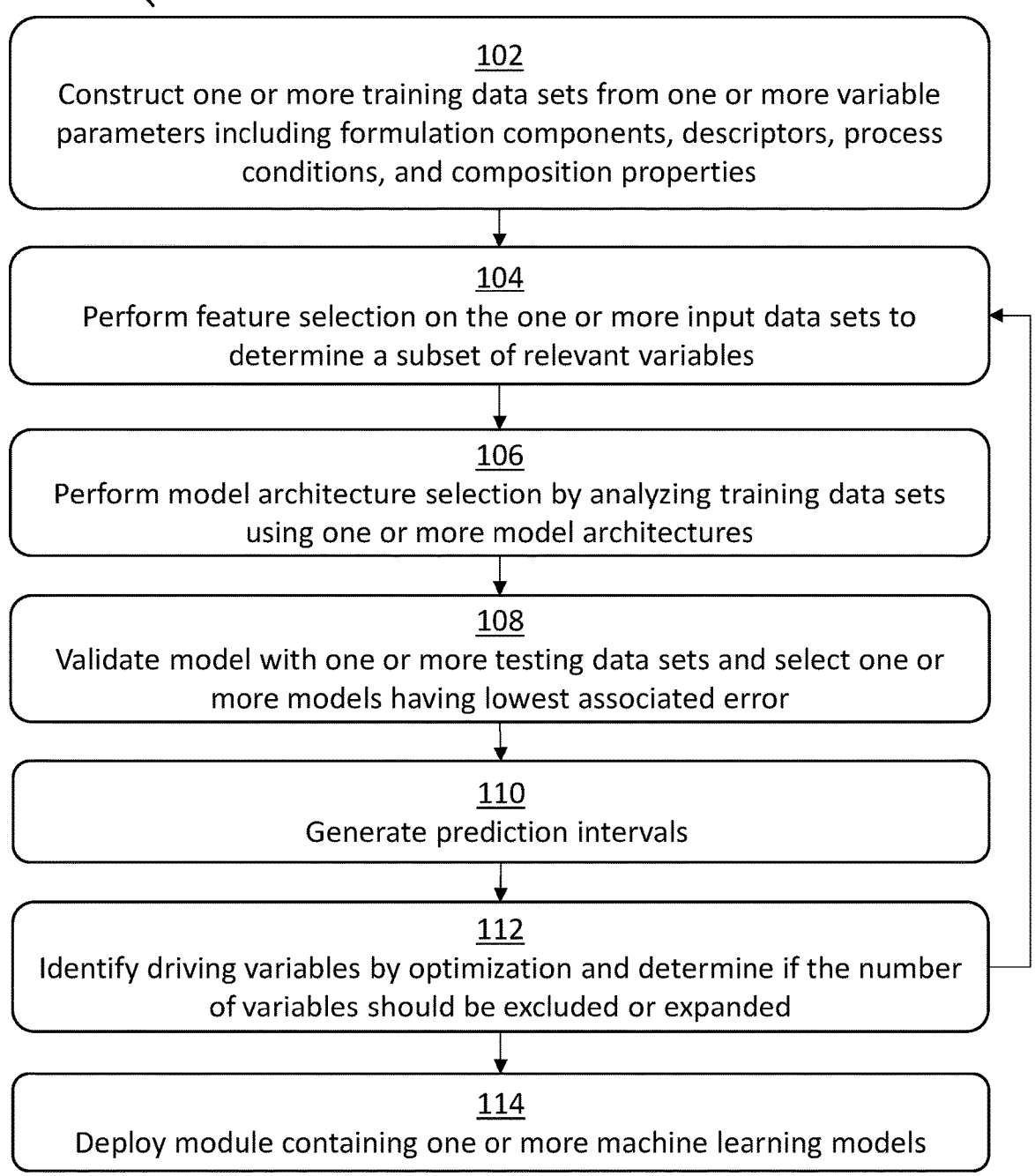
FIG. 1 is a flow diagram illustrating a method of training a machine learning module to predict target product properties of a chemical formulation.

Embodiments relate to methods of training a machine learning module containing one or more models using machine learning using a hybrid model approach that combines composition-based, process conditions, and physics-based methodologies that result in increased prediction accuracy (e.g., $R^2$) of predicted target product properties (e.g., foam density, tensile properties, hardness) from prospective chemical formulations. Methods of training a machine learning module may include generating train and test data sets containing chemical formulation data (historical and/or hypothetical) and selective descriptors that account for chemical and structural relationships, which are then used to select and optimize one or more machine learning model architectures for calculating one or more predicted target product properties. Methods may also include inputting a prospective formulation into a trained machine learning module and generating a predicted target product property (or properties) of interest, which may be applied to the design of chemical formulations and/or products.

As used herein, "machine learning modules" refers to a software package that may include one or more machine learning models, which are trained, or capable of being trained, to estimate a target product property given an input, such as a test or experimental data set.

As used herein, "formulations" refers to combination of components (e.g., polymer compositions, reactant mixtures, blends, etc.) for product applications.

As used herein, "component" refers to chemical species and/or chemical classifications (e.g., including but not limited to monomers, prepolymers, chemical species containing none, one or more reactive groups, catalysts, etc.).

As used herein, "process conditions" (e.g., atmospheric pressure, variable pressure foaming, relative humidity, overpacking percentage, etc.) refers to an expression describing the process conditions affecting the properties.

As used herein, "descriptor" (e.g., monomer mw, water content, catalytic activity, polymer chain entanglement, etc.) refers to an expression describing a correlation within a chemical system that can provide additional information and/or generalizations regarding system behaviors Descriptors herein may be calculated from component information and concentration using various physics-based approaches and models target product properties As used herein, "target product property" refers to a property associated with a unique chemical formulation (e.g., chemo-rheology, foam density, hardness, modulus, etc.) that is selected based on desired user input for a given product application. Target product properties may be obtained from historical data and used to train a machine learning module. When trained, machine learning modules may then generate predicted target product properties from an input of a prospective chemical formulation. In some cases, the determination of multiple target product properties by a machine learning module may be done simultaneously, in series, in parallel, or any other suitable subcombination.

As used herein, "variable parameter" refers to a feature of a machine learning module and/or model that can be varied during training (e.g., chemical species and/or class, concentration, descriptor value, etc.).

Methods disclosed herein may include a hybrid machine learning approach that combines composition-based, process conditions and physics-based methodologies that result in increased prediction accuracy (e.g., $R^2$) of predicted target product properties (e.g., foam density, tensile properties, hardness) from prospective chemical formulations. Machine learning modules disclosed herein may enable developers to explore chemical space for hundreds of formulations virtually, saving time and resources by validating smaller numbers of prospective formulations by experiment. In some cases, predicted target product properties generated from machine learning modules trained according to the present disclosure may be part of a larger control process that enables an operator to adjust a formulation and/or process conditions generating a product, or reject a formulation based on the predicted target product property. Predicted target product properties generated from a trained machine learning module may be calculated in "real time" such as less than 10 minutes, for example. Machine learning modules may also be updated in real-time as the training database is updated and/or when the module generates new data.

Hybrid modeling approaches may combine composition information, process conditions, physics-based methodologies and machine learning methodologies to process experimental data (historical data) to identify patterns and predict targeted product properties. Previous approaches relying solely on compositional information utilize training data sets assembled from historical chemical formulation data containing components (e.g., chemical identities and/or classes) and their concentrations (e.g., percent by weight (wt %)), along with associated resulting target product properties. The training data set is then used to train one or more models using machine learning methodologies to develop a trained machine learning module capable of estimating predicted target product properties from an input prospective formulation. However, composition-based models require access to large data sets of formulations (e.g., tens of thousands, millions) and measurement data to adequately model interactions and predict target product properties.

Other approaches include descriptor-based methodologies that utilize historical formulation data to calculate various physical descriptors that may be general or specific to a particular chemical field or application. For example, general descriptors may include component molecular weight, ionic charge, and functional group number, while specific descriptors (relevant to polyurethanes and polyurethane foams in this case) may include NCO index, OH number, functionality, equivalent weight, molecular weight, molar volume, computed polar surface area, number of hydrogen bond acceptors, partition coefficient, water content, solids, etc. Descriptors may be calculated using known physical relationships, such as equilibrium thermodynamics, Gibson-Ashby for simple foam mechanics, and the like. Descriptor-based methodologies provide some utility in the prediction of bulk properties (e.g., density) with reasonable correlation with experimental results.

Particularly, when limited data sets are available, it is challenging to develop machine learning models to predict target product properties from a prospective formulation. Previous modeling approaches also lack the required accuracy and precision for many target properties, such as foam density, compressive strength, compression force deflection (CFD), and the like.

Hybrid model approaches disclosed herein include training a machine learning model or module with a training data set containing a mixed input containing chemical formulation information and descriptor information. In some cases, hybrid methodologies may be useful for cases in which small numbers of historical chemical formulation data are available (e.g., <3,000). FIG. 1 (100) provides a general overview of a hybrid modeling approach used to train a machine learning module to predict target product properties from a prospective formulation input. At 102, a training data set is created for one or more variable parameters from historical formulation data, which may include formulation components, process conditions, and one or more associated target product properties. Chemical formulation information may include various chemical components included in a formulation, in addition to the concentration of the component in terms of amount or ranges. The training data set generated at 102 can also include other attributes such as process parameters (e.g., temperature, pressure, pH), the conditions at the beginning of the production process and the conditions at the end of the production process, and the like. Target product properties are application specific and may be intrinsic or extrinsic features such as physical properties (e.g., density, compression force deflection, resilience, tear strength, sag, particle size, cell size, adhesion, tackiness, etc.) and/or appearance (e.g., morphology, gloss, roughness).

Training data sets may also include one or more descriptors generated by converting component physical properties and concentrations (e.g., wt %) to descriptors (e.g., OH-number, NCO, functionality, etc.) using suitable physics-based models/tools known in the art. Descriptors disclosed herein are computed from the properties of the individual components in the formulation, such as by using a physics model suited for the particular chemical application (e.g., polyurethane compositions). Descriptors may contain data regarding formulation components, component concentrations and ratios, such as ratios of polyurethane reactants (e.g., the ratio of the isocyanate component and polyol component), product generating reactions among components, and properties result from various chemical interactions (e.g., functionality for isocyanates or reactive species, crosslinking, blowing agent reactivity). Suitable descriptors also include those detailing mechanical properties, such as vapor heat capacity, foam density, Young's modulus, rheology properties, heat transfer properties, and the like. In some cases, training data sets may include one or more variable parameters that include one or more descriptors (e.g., descriptors generated by physics-based models and/or relating to polyurethane formulations or foams), and one or more of chemical components, process conditions, and target product properties.

At 104, feature selection is performed on the training data set constructed in 102. During feature selection, a subset of the variable parameters identified in the training set are identified as "driving" variables affecting the targeted product property. Feature selection may then involve the exclusion of irrelevant, noisy, and redundant features from the training data set.

Feature selection techniques may include one or more of descriptor feature selection; removing constraining features; correlation testing methods such as Pearson, Spearman, Kendall, and the like; analysis of variance (ANOVA) univariate testing; mean absolute different testing; L1 or Least absolute shrinkage and selection operator (Lasso) regularization; multivariate analysis (baseline); and the like.

At 106, machine learning model architecture is surveyed by training one or more machine learning models with the driving variables established from 104 as input. The generated machine learning models from the surveyed architectures are then compared and rated for accuracy, which is then used to select one or more model architectures used in subsequent stages. For example, a machine learning module may output one or more predicted product properties from a prospective chemical formulation. In some cases, more than one trained machine learning model may be combined into a machine learning module, where the output is the result of constituent machine learning model having higher accuracy for the selected target product property and/or is the result of averaging the output of one or more machine learning models in the module.

Suitable machine learning modules may include artificial neural networks such as deep neural networks (DNNs), symbolic regression, recurrent neural networks (RNNs) that include long short-term memory (LSTM) networks or Gated Recurrent Unit (GRU) networks, decision trees, random forests, boosted trees such as gradient boosted trees (XG-Boost), linear regression, partial least squares regression, support vector machines, multilayer perceptron (MLP), autoencoders (e.g., denoising autoencoders such as stacked denoising autoencoders), Bayesian networks, support vector machines (SVMs), hidden Markov models (HMNIs), and the like. Commercially available software packages may include JMP software, Microsoft AzureML, SAP data analysis tools, soft independent modeling by class analogy (SIMCA) by Sartorius, and the like.

Machine learning architectures may also utilize deep learning in which a neural network is generated with multiple layers. These layers extract successively higher order features from a training data set. For chemical formulations, examples of layers containing lower order features may include general classifications of component type, while layers including higher order features in the network may include details dependent on functional groups, ionization state, charge, and the like.

At 108, the method further includes training and validating multiple models with a testing data set containing the variable data and target formulation property data, and then selecting an appropriate model based on desired model criteria such as best fit according to error calculation techniques such as $R^2$, mean associated percent error (MAPE), root mean squared error (RMSE), and the like. The testing data set may contain chemical formulation information and descriptor information that is similar in structure to the training data set, however, it usually contains sample information that is minimally duplicative to the training data in order to provide an adequate test of the ability of the machine learning module to handle new information, as opposed to storage and retrieval of the training data set values.

Underfitting is a scenario where a model cannot capture the relationship between the input and output variables. In the case of $R^2$-based methods, the underfitted models tend to have undesirably low training $R^2$. The training $R^2$ threshold may be set at a desired accuracy to filter out underfit models, such as greater than 0.70, 0.85, 0.88, or 0.9. Further, overfit models may occur in which the model is too closely aligned to the training data, and the learned representation cannot predict the validation data accurately. In some cases, error calculation techniques may also be used to select for generalizable models while filtering out overfitted models. For example, validation percentage RMSE threshold of less than 40%, 35%, or 30% may be used to predict target product properties.

In some cases, parameters for the model are optimized by minimizing the mean squared error (MSE) between the actual value $y_i$ and the predicted value $\hat{y}_i$, as shown in equation (I) below:

$$MSE = \frac{1}{n}\sum_{i=1}^{n}(y_i - \hat{y}_i)^2 \tag{I}$$

where n is the total number of data points, $y_i$ is the actual value of the target product property measured, i is the sample data point, and $\hat{y}_i$ is the model predicted value of the target product property.

MSE is a metric used to measure the average of the squares of the difference between the predicted values and the actual values. RMSE means root mean squared error that is a metric to measure the difference between the predicted values and the actual values. Percentage RMSE is the square root of MSE normalized by the population mean to a dimensionless number expressed as a percentage. The percentage RMSE can be calculated as below:

$$\text{percentage } RMSE = \frac{\sqrt{\sum_i^n \frac{(\hat{y}_i - y_i)^2}{n}}}{\overline{y}_i} \times 100 \qquad \text{(II)}$$

where n, $y_i$, i and $\hat{y}_i$ are as defined above in equation (I) above, and $\overline{y}_i$ is the mean value for the target product property measured. The lower the percentage RMSE, the better the model fits a dataset.

$R^2$ means the coefficient of discrimination, which is a commonly used performance metric for regression that calculates the proportion of variance explained by a regression model. $R^2$ normally ranges from 0 to 1 and can be calculated according to equation (III) below:

$$R^2 = 1 - \frac{\sum_i (y_i - \hat{y}_i)^2}{\sum_i (y_i - \overline{y}_i)^2} \qquad \text{(III)}$$

where $y_i$, i and $\hat{y}_i$ are as defined above in equation (I) above, and $\overline{y}_i$ is the mean value. The higher the $R^2$, the better the model fits a dataset.

In one embodiment, the method can provide predictions for target product properties of a formulation chemical composition, as indicated by "training $R^2$>0.70" as calculated according to the equation (III) above, and test percentage RMSE less than 30% (<30%) as calculated according to the equation (II) above. In addition, validation percentage RMSE is <30% as calculated according to the equation (II) above. "Training $R^2$" refers to $R^2$ for the training dataset, "validation percentage RMSE" refers to the percentage RMSE for the validation dataset, and "test percentage RMSE" refers to the percentage RMSE for the test dataset.

At 110, prediction intervals are generated for the created models using bootstrapping (bagging) or ensembling methodologies to provide a measure of the probable error for target formulation property predictions. For example, prediction intervals may be represented as range of variance around the associated mean value. During bootstrapping, samples are drawn from the training data and input into a model, and the results are combined by averaging for regression and simple voting for classification, to obtain the overall prediction.

At 112, model optimization is used to identify driving variables to determine whether the obtained model accuracy is increased by removing or adding additional variables. Optimization methods may evaluate how significant each selected variable is in determining the prediction of the model outputs. The subset of variables having the greatest impact on model accuracy can then be used to determine if training process 100 is complete (e.g., prediction accuracy acceptable), or should be reiterated by repeating 104 to 112. In some cases, iterations may be repeated multiple times such as 2 to 3 or more.

Optimization methods may evaluate the selected variables on the target product properties output from the models and processed using interpreting and explanatory software, such as SHapley Additive ex-Planation (SHAP), Local Interpretable Model-Agnostic Explanations (LIME), Variable Importance to the Projection (VIP), and the like. For example, SHAP analysis assigns each input variable an important value for a particular prediction by comparing a model's output with and without a specific variable. SHAP values are then computed using a sum that represents the impact of each input variable added to the model averaged over all possible orderings of variable being introduced. Positive SHAP values indicate that higher feature values lead, on average, to higher predicted values, while negative SHAP values indicate that lower feature values lead, on average, to lower predicted values.

Optimization methods 112 may further include pruning a machine learning module/model by removing variable parameters that do not contribute to the one or more target formulation properties calculated.

In some cases, machine learning modules disclosed herein may include one or more machine learning models trained to obtain a prediction accuracy as calculated by $R^2$ for at least one target formulation property of at least 0.70, at least 0.75, or at least 0.80.

Figure 2:
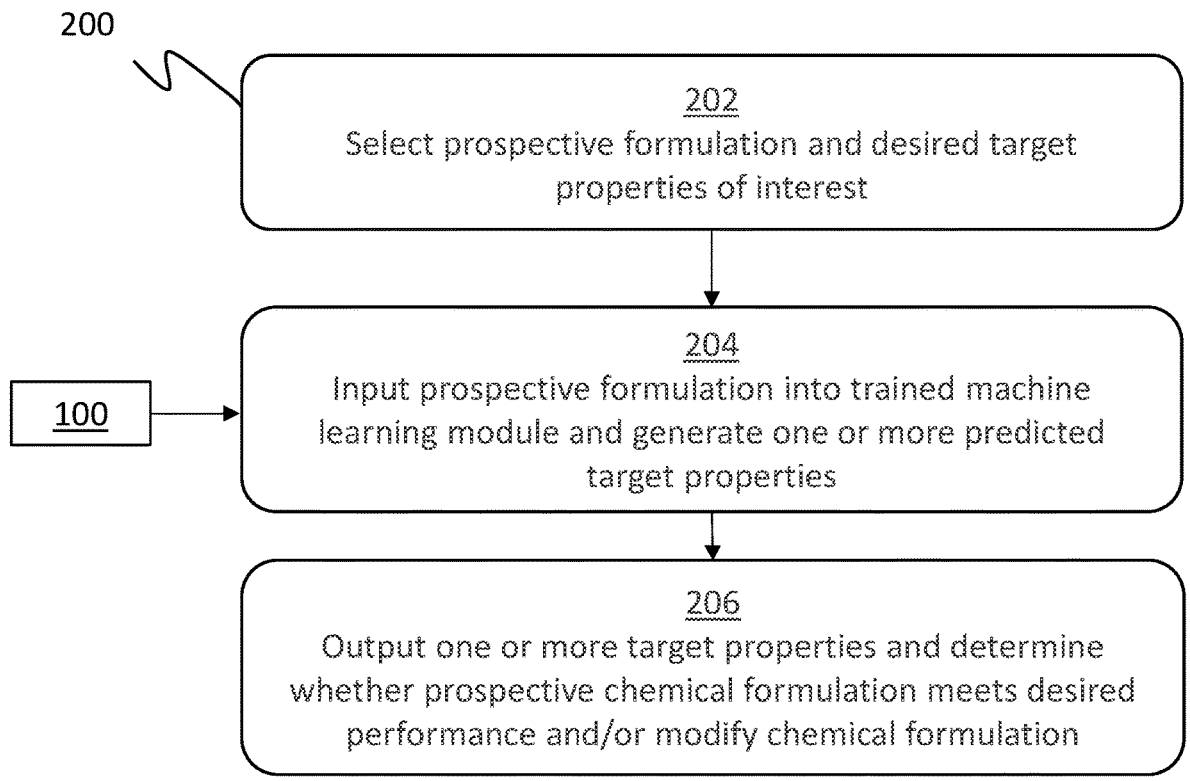
FIG. 2 is a flow diagram illustrating a method of predicting one or more target product properties for a prospective chemical formulation.

At 114, the optimized and trained machine learning module is deployed and used to generate predicted target product properties for a prospective chemical formulation. FIG. 2 illustrates a method of using a trained machine learning module to generate one or more target product properties from a prospective chemical formulation. At 202, one or more prospective formulations are selected and input into a trained machine learning module to calculate one or more predicted target product properties at 204.

At 206, one or more predicted target product properties are generated simultaneously as an output. The predicted properties may be used to determine whether prospective chemical formulation meets desired performance criteria, or whether further modifications to the formulation or article production process should be made. Target product property output may also be used to evaluate a produced product or article, allowing an operator to accept or reject a product produced from the prospective chemical formulation and/or chemical process. Modifications may include inclusion or removal of chemical components or various additives, modifying process parameters such as reaction temperatures, concentrations, reactor design, pressure and the like. For example, predicted target product properties may be included adjusting a polyurethane-forming reaction to include more or less catalyst to control target product properties such as density and hardness.

In some cases, a user may utilize an interface that enables the selection of formulation components, respective concentrations, and target product property (or properties) of interest. Once the desired criteria are input, the machine learning module provides a prediction of the target product property. The target product property generated may then be used to inform one or more of whether the prospective chemical formulation should be further adjusted to meet the desired target product property, whether a process for generating a formulation or reaction product should be adjusted, and whether a produced product meets the expected criterion.

Computer systems disclosed herein may output one or more target product properties for a prospective formulation such as chemical formulations, material combinations, catalyst mixtures, and the like. Computer systems may include a processor and data storage, where the data storage has stored thereon computer-executable instructions that, when executed by the processor, cause the computing device to carry out functions. Computing devices may include a client device (e.g., a device actively operated by a user), a server device (e.g., a device that provides computational services to client devices), or some other type of computational platform. Some server devices can operate as client devices from time to time in order to perform particular operations, and some client devices can incorporate server features.

The processor useful in the present disclosure can be one or more of any type of computer processing element, such as a central processing unit (CPU), a co-processor (e.g., a mathematics, graphics, neural network, or encryption co-processor), a digital signal processor (DSP), an application specific integrated circuit (ASIC), a network processor, and/or a form of integrated circuit or controller that performs processor operations.

The data storage can include one or more data storage arrays that include one or more drive array controllers configured to manage read and write access to groups of hard disk drives and/or solid-state drives.

Computing devices may be deployed to support a clustered architecture. The exact physical location, connectivity, and configuration of these computing devices can be unknown and/or unimportant to client devices. Accordingly, the computing devices can be referred to as "cloud-based" devices that can be housed at various remote data center locations, such as a cloud-based server cluster. Desirably, the computing device is a cloud-based server cluster and inputting the concentration data to the model via a web-based user interface where users can get access.

Figure 3:
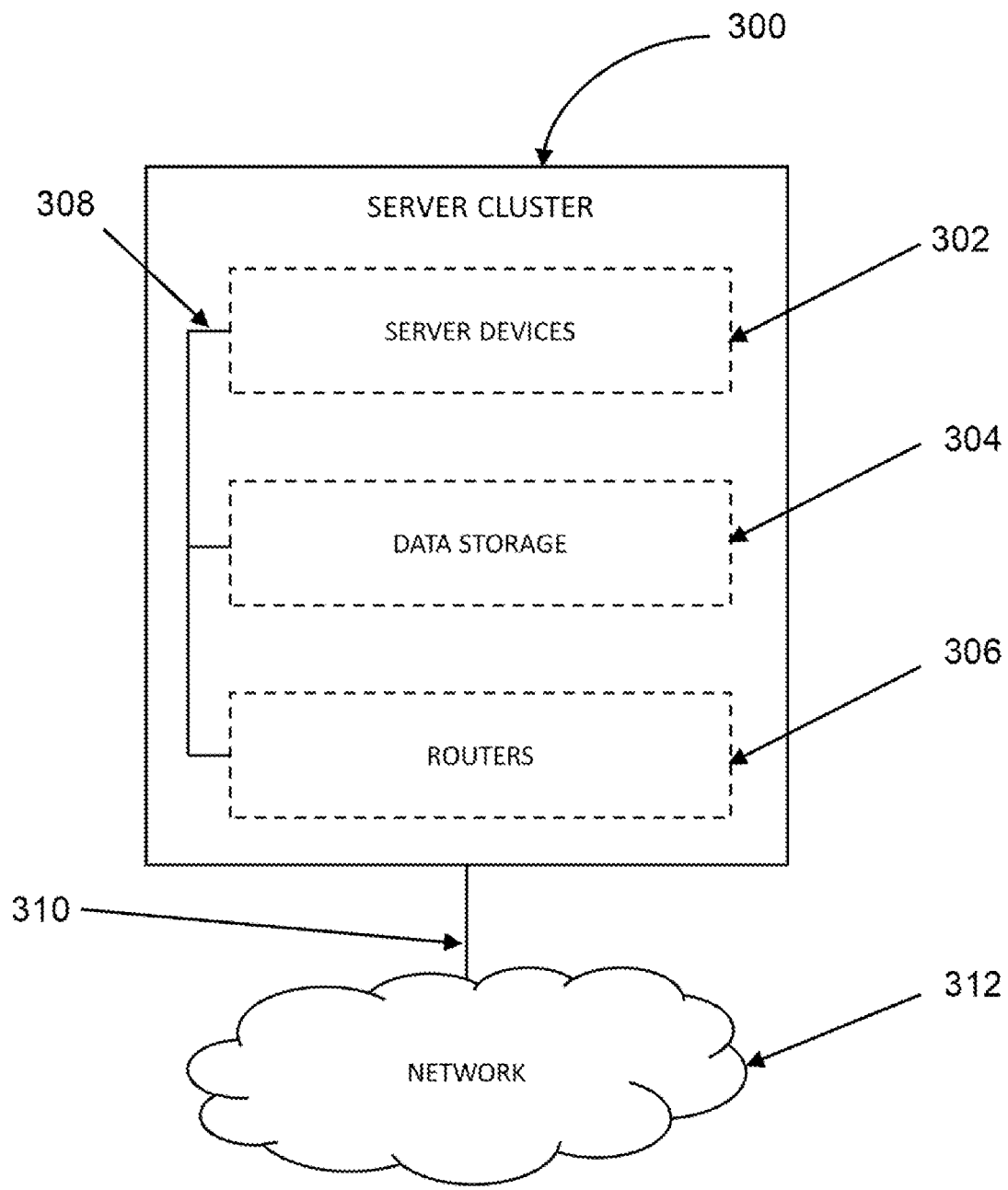
FIG. 3 illustrates a schematic drawing of a cloud-based server cluster in accordance with one example of the present disclosure.

FIG. 3 depicts a schematic drawing of a cloud-based server cluster 300 in accordance with one example of the present disclosure. Desirably, operations of a computing device can be distributed between server devices 302, data storage 304, and routers 306, all of which can be connected by local cluster network 308. The amount of server devices 302, data storage 304, and routers 306 in the server cluster 300 can depend on the computing task(s) and/or applications assigned to the server cluster 300. For example, the server devices 302 can be configured to perform various computing tasks of the computing device. Thus, computing tasks can be distributed among one or more of the server devices 302. As an example, the data storage 304 can store any form of database, such as a structured query language (SQL) database. Furthermore, any databases in the data storage 304 can be monolithic or distributed across multiple physical devices. The routers 306 can include networking equipment configured to provide internal and external communications for the server cluster 300. For example, the routers 306 can include one or more packet-switching and/or routing devices (including switches and/or gateways) configured to provide (i) network communications between the server devices 302 and the data storage 304 via the cluster network 308, and/or (ii) network communications between the server cluster 300 and other devices via the communication link 310 to the network 312. The server devices 302 can be configured to transmit data to and receive data from cluster data storage 304. Moreover, the server devices 302 can have the capability of executing various types of computerized scripting languages, such as Perl, Python, PHP Hypertext Preprocessor (PHP), Active Server Pages (ASP), or JavaScript. Computer program code written in these languages can facilitate the providing of web pages to client devices, as well as client device interaction with the web pages.

EXAMPLES

The following example is provided to illustrate an embodiment applied to predict a number of target product properties for a polyurethane chemical formulation, but is not intended to limit the scope thereof this disclosure. It is envisioned that methodologies in accordance with the present disclosure are not limited to polyurethanes and may be adapted to predict target product properties in other chemical areas and applications.

In this example, a module trained by hybrid model methodology in accordance with the present disclosure (I1) is analyzed with comparative modules trained used a composition-based model (C1) or a descriptor-based model (C2) to determine target product properties for a polyurethane foam formulation. A machine learning module containing several machine learning models trained and used to determine a number of target product properties for a polyurethane foam formulation including density, compressive force deflection (CFD at 25%, 40%, and 65%, resilience, tear strength, and CFD Sag.

Data for the formulation components were gathered from ~3,000 historical formulations and associated foam properties. The formulation components were subdivided into classes by chemical type, including polyol, isocyanate, catalysts, surfactants, blowing agents, and additives.

The composition-based models were then trained using machine learning with this training data set, which included selected formulation components, concentrations, and associated foam properties.

Descriptor-based models utilized a first processing stage in which physics-based models are used to generate relevant polyurethane-specific descriptors using physics-based models and the underlying formulation component and concentration data. The descriptor-based models was then trained using machine learning with a training set that included the descriptors and associated foam properties.

The training data sets for the composition- and descriptor-based models were combined and used to train models using machine learning or the hybrid model as discussed above.

TABLE 1

Relevant variable parameters
Features of formulation components

OH-Number for polyols
NCO index for isocyanates
Functionality for polyols and isocyanates
EW for polyols and isocyanates
MW for polyols and isocyanates
SMILES for small molecules in the formulations (for E.g., catalysts and blowing agents)
Molar Volume for small molecules in the formulations (for E.g., catalysts and blowing agents)
Computed polar surface area for small molecules in the formulations (for E.g., catalysts and blowing agents)
No. of Hydrogen bond acceptor for small molecules in the formulations (for E.g., catalysts and blowing agents)
Partition Coefficient (CLogP) for small molecules in the formulations (for E.g., catalysts and blowing agents)
Water Content in polyols and additives
% Solids in polyols
Percent ethylene oxide in polyol or prepolymer (EO %)
Primary OH content of polyols
Number of Hydrogen bond donor for small molecules in the formulations (for E.g., catalysts and blowing agents)

Formulation descriptors used to train models using machine learning are dependent on the target product properties to be predicted, the available historical data sets, and the nature of the chemical components. The computed formulation descriptors for predicting polyurethane foam properties disclosed herein include one or more of the following: sum of polyol parts in polyol blend; weight % of blowing agent class in formulation; weight % of isocyanate in isocyanate blend; averaged polyol glass transition temperature; averaged polyol solid phase modulus; average entanglement mw; average functionality; average molar mass (g/mol); average polyol glass transition temperature; average polyol solubility parameter; average Williams-Landel-Ferry Equation C1 constant; average Williams-Landel-Ferry Equation C2 constant; average polyol equivalent weight (g/mol); average polyol functionality; average Equivalent weight of Polyols plus Water (g/mol); average Equivalent weight of Isocyanates (g/mol); weight averaged hydrogen bond acceptor of additives; weight averaged hydrogen bond donor of additives; weight averaged computed water/octanol partition coefficient of additives; weight averaged molar volume of additives; weight averaged MW of additives; weight averaged total polar surface area of additives; weight averaged hydrogen bond acceptor of blowing agents; thermal conductivity of blowing agents; weight averaged hydrogen bond donor of blowing agents; weight averaged computed water/octanol partition coefficient of blowing agents; weight averaged molar volume of blowing agents; weight averaged MW of blowing agents; weight averaged total polar surface area of blowing agents; weight averaged hydrogen bond acceptor of catalyst; weight averaged hydrogen bond donor of catalyst; weight averaged computed water/octanol partition coefficient of catalyst; weight averaged molar volume of catalyst; weight averaged MW of catalyst; weight averaged total polar surface area of catalyst; weight averaged hydrogen bond acceptor of chain extender; weight averaged hydrogen bond donor of chain extender; weight averaged computed water/octanol partition coefficient of chain extender; weight averaged molar volume of chain extender; weight averaged MW of chain extender; weight averaged total polar surface area of chain extender; class of blowing agent; Boiling Point (° C. @760 mmHg); broad isocyanate class (MDI or TDI); total number of catalyst; total number of chain extender; volume equivalent of $CO_2$ of the formulation in cc/g; Moles of carbon dioxide assuming full reaction of water; weight averaged water coming from the polyol side; crosslink functionality; average density of ISO side; average density of polyol side; percentage of ethylene oxide in the polyol side; excess of isocyanates (moles); density of fluid (g/cm3) at 25° C.; foam classification (e.g. conventional foam); foam shear modulus (mPa); theoretical foam density (kg/m3); free isocyanate equivalent number (moles); percentage of the hard segments in segmented representation of a polyurethane network; number of hydrogen bond acceptor; number of hydrogen bond donor; polyol/iso ratio; part ratio isocyanate blend/polyol blend (physical blowing agent included); number of isocyanates; equivalent number of isocyanate converted to trimer; weight averaged heat capacity for molecular ingredients; weight percentage of the hard segments in segmented representation of a polyurethane network; weight fraction of methylene chloride; weight averaged group contribution based water octanol partition coefficient for molecular ingredients; weight averaged MW of the molecular ingredients; weight averaged NCO content in a formulation; weight averaged OH content in a formulation; MW between crosslink (g/mol); Percentage of isocyanate moles converted at gel point; isocyanate index; weight averaged functionality of polyols side; number of physical blowing agents; number of nitrogen atoms in catalyst; average OH equivalent numbers of polyols (moles); average OH equivalent numbers of polyols including water (moles); percentage of OH equivalent number converted at Gel Point; Percentage of OH equivalent number converted at gel point; polyols hydroxyl number; parts by weight of isocyanate based on parts per hundred of polyol (pphp); number of moles of physical blowing agent; part ratio polyol blend/isocyanate blend (physical blowing agent included); part ratio polyol blend/isocyanate blend (physical blowing agent included); average OH equivalent numbers of polyols (moles); average OH Equivalent numbers of polyols and water (moles); weight averaged primary OH content in the formulation; total number of chemical blowing agent; theoretical foam resiliency; sum of OH equivalent number of polyols in polyol blend (moles); sum of OH equivalent number in polyol blend (moles); sum of NCO equivalent number in isocyanate blend (moles); total number of silicones; weight averaged solid content in polyols; average density of the formulation (excluding all formed gas); sum of equivalent numbers of crosslinks; total amount of additives; total amount of catalysts; total amount of chain extenders; total amount of crosslinkers; total amount of isocyanates; total amount of physical blowing agents; total amount of polyol side; total amount of chemical blowing agents; lower bound of loss tangent (usually a constant); loss tangent (which is a function of temperature and hard segment content); flexible slab-stock foam technology; Total amount of water (water as blowing agent+extra water from component); total volume ($cm^3$) of gas per g of formulation; total volume (cm3) of gas per gram of formulation; weight averaged total polar surface area; total amount of equivalents; total amount of urea links (moles); weight averaged vapor density (relative to air=1) of the molecular components; weight averaged vapor heat capacity (J/molK near 25° C.) of molecular components; weight averaged viscosity (cP near 25° C.) of the molecular components; weight averaged 3D volume of the molecular material; averaged functionality of the formulation assuming stoichiometric and full conversion; and Young's modulus of crosslinked PU.

For the hybrid-based model, SHAP analysis was used to determine approximately <50 descriptors having the greatest impact for the respective target product property, while irrelevant descriptors were removed from the model.

Composition data and relevant associated formulation descriptors were used to explore various machine learning model architectures, which includes decision tree-based architectures, dense NN architectures and linear regression models. The model accuracy was evaluated on a separate hold out test set for each property of interest. The accuracy of the best hybrid models is higher than composition only model and can be used as predictive model for new compositions.

TABLE 2

Prediction accuracy for machine learning modules

| Target formulation Property | Model Architecture | C1 Descriptor-based machine learning Model ($R^2$) | C2 Composition-based machine learning Model ($R^2$) | I1 Hybrid Model ($R^2$) |
|---|---|---|---|---|
| Density | Boosted NN Model | 0.92 | 0.90 | 0.93 |
| CFD-25% | Boosted NN Model | 0.78 | 0.69 | 0.87 |
| CFD-40% | Boosted NN Model | 0.77 | 0.75 | 0.86 |
| CFD-65% | Combination of Boosted NN and XGBoost Regressor | 0.76 | 0.74 | 0.81 |
| Resilience | XGBost | 0.95 | 0.92 | 0.95 |

TABLE 2-continued

Prediction accuracy for machine learning modules

| Target formulation Property | Model Architecture | C1 Descriptor-based machine learning Model ($R^2$) | C2 Composition-based machine learning Model ($R^2$) | I1 Hybrid Model ($R^2$) |
|---|---|---|---|---|
| Tear Strength | XGBoost Regressor | 0.83 | 0.82 | 0.83 |
| CFD Sag | XGBoost Regressor | 0.63 | 0.54 | 0.74 |

While the foregoing is directed to exemplary embodiments, other and further embodiments may be devised without departing from the basic scope thereof, and the scope thereof is determined by the claims that follow.

The invention claimed is:

1. A method of training a machine learning module to predict one or more target product composition properties for a prospective polyurethane chemical formulation, comprising:
  (a) constructing or updating a training data set from variable parameters comprising at least one selected from each of:
    (i) one or more of chemical components and process conditions,
    (ii) one or more polyurethane specific descriptors, and
    (iii) the one or more target product composition properties;
  (b) performing feature selection on the training data set to determine a subset of driving variable parameters for calculating the one or more target product properties, wherein the subset of driving variable parameters comprises at least one polyurethane specific descriptor;
  (c) building one or more machine learning models using one or more model architectures and analyze the training data set and subset of driving variable parameters used in calculating the one or more target product properties, wherein the subset of driving variable parameters comprises at least one selected from a group consisting of hydroxyl number for polyols, isocyanate index, weight averaged solids content in polyol, total amount of additives, primary hydroxyl content of polyols, and total amount of crosslinkers;
  (d) validating the one or more machine learning models by inputting a testing data set and determining an associated error for the one or more machine learning models calculating the one or more target product properties;
  (e) selecting at least one of the one or more machine learning models and generating prediction intervals for the one or more machine learning models;
  (f) interpreting the one or more machine learning models and analyzing the one or more target product properties calculated by the one or more machine learning models;
  (g) determining if the one or more target product properties calculated by the one or more machine learning models are acceptable based on pre-defined criteria; and
  (h) deploying one or more trained machine learning models;

wherein the method is performed by one or more processors.

2. The method of claim 1, wherein the prediction intervals are generated using a bootstrapping or ensemble method.

3. The method of claim 1, wherein the associated error of (d) is determined by one or more of MAPE, $R^2$, and RMSE.

4. The method of claim 1, wherein the one or more model architectures is selected from one or more of selected from neural networks, symbolic regression, decision trees, random forests, boosted trees, linear regression, partial least squares regression, support vector machines, multilayer perceptron, Bayesian networks, and hidden Markov models.

5. The method of claim 1, wherein the model outputs are evaluated using Shapley additive explanation (SHAP), local interpretable model-agnostic explanation (LIME), or Variable Importance to the Projection (VIP).

6. The method of claim 1, wherein (f) further comprises pruning the one or more machine learning models by removing variable parameters that do not contribute to the one or more target product properties calculated.

7. The method of claim 1, wherein (f) further comprises introducing additional variable parameters into the one or more machine learning models and repeating steps (b) to (f).

8. The method of claim 1, wherein the one or more trained machine learning models have a prediction accuracy as calculated by $R^2$ of at least 0.75.

9. The method of claim 1, further comprising optimizing the one or more machine learning models by repeating steps (b) to (f).

10. The method of claim 1, wherein the polyurethane specific descriptors comprise one or more of a group of polyurethane specific descriptors including NCO index, OH number, functionality, equivalent weight, molecular weight, molar volume, computed polar surface area, number of hydrogen bond acceptors, partition coefficient, water content, and solids content.

11. The method of claim 1, wherein the target product composition properties are selected from at least one of density, compressive force deflection, resilience, tear strength, and compressive force deflection sag.

12. The method of claim 1, wherein the subset of driving variable parameters further comprises water content.

13. A method of determining one or more target product composition properties from a prospective polyurethane chemical formulation, comprising:
inputting the prospective chemical formulation into a trained machine learning module, wherein training the trained machine learning module comprises:
  (a) constructing or updating a training data set from variable parameters comprising at least one selected from each of:
    (i) one or more of chemical components and process conditions,
    (ii) one or more polyurethane specific descriptors, comprising expressions describing a correlation within a chemical system that provide information regarding behavior of the chemical system, and
    (iii) the one or more target product composition properties;
  (b) performing feature selection on the training data set to determine a subset of driving variable parameters for calculating the one or more target product properties, wherein the subset of driving variable parameters comprises at least one polyurethane specific descriptor selected from a group consisting of hydroxyl number for polyols, isocyanate index, weight averaged solids content in polyol, total amount of additives, primary hydroxyl content of polyols, and total amount of crosslinkers;

(c) building one or more machine learning models using one or more model architectures and analyze the training data set and subset of driving variable parameters used in calculating the one or more target product properties;

(d) validating the one or more machine learning models by inputting a testing data set and determining an associated error for the one or more machine learning models calculating the one or more target product properties;

(e) selecting at least one of the one or more machine learning models and generating prediction intervals for the one or more machine learning models using a bootstrapping method;

(f) interpreting the one or more machine learning models and analyzing the one or more target product properties calculated by the one or more machine learning models;

(g) determining if the one or more target product properties calculated by the one or more machine learning models are acceptable and deploying one or more trained machine learning models;

inputting a selection of one or more target product properties to be predicted into the machine learning module; and outputting the one or more predicted target product properties;

wherein the method is performed by one or more processors.

14. The method of claim 13, further comprising accepting or rejecting a product produced from the prospective chemical formulation and/or modifying a process generating the product based on the one or more predicted target product properties.

15. The method of claim 13, wherein the one or more trained machine learning modules have a prediction accuracy as calculated by $R^2$ of at least 0.75.

16. The method of claim 13, further comprising optimizing the one or more machine learning models by repeating steps (b) to (f).

17. The method of claim 13, wherein performing feature selection on the training data set to determine a subset of driving variable parameters comprises selecting at least one chemical classification from the one or more chemical components.

18. The method of claim 13, wherein the polyurethane specific descriptors comprise one or more of a group of polyurethane specific descriptors including NCO index, OH number, functionality, equivalent weight, molecular weight, molar volume, computed polar surface area, number of hydrogen bond acceptors, partition coefficient, water content, and solids content.

19. The method of claim 13, wherein the target product composition properties are selected from at least one of density, compressive force deflection, resilience, tear strength, and compressive force deflection sag.

20. The method of claim 13, wherein the subset of driving variable parameters further comprises water content.

* * * * *